Figure 1:
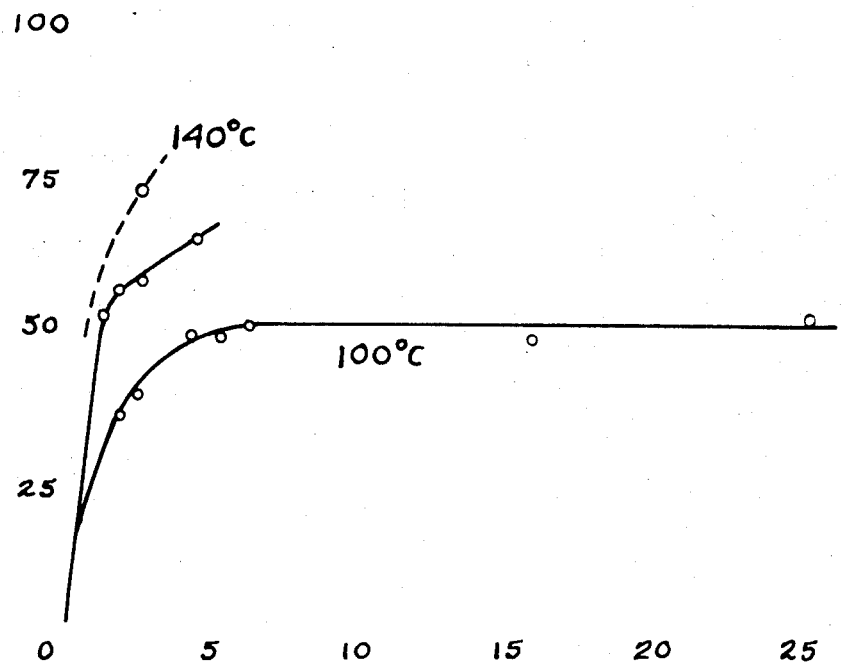

United States Patent [19]

Barr et al.

[11] 4,232,142
[45] Nov. 4, 1980

[54] PRODUCTION OF POLYARYLENE ETHER SULPHONES AND KETONES

[75] Inventors: Dennis A. Barr, Welwyn; John B. Rose, St. Albans, both of England

[73] Assignee: Imperial Chemical Industries Limited, Great Britain

[21] Appl. No.: 632,979

[22] Filed: Nov. 18, 1975

Related U.S. Application Data

[60] Division of Ser. No. 335,902, Feb. 26, 1973, Pat. No. 4,051,109, which is a continuation-in-part of Ser. No. 580,290, Sep. 19, 1966, abandoned.

[30] Foreign Application Priority Data

Sep. 24, 1965 [GB] United Kingdom ............... 40734/65
Jan. 31, 1966 [GB] United Kingdom ............... 4176/66
Jan. 31, 1966 [GB] United Kingdom ............... 4177/66
Jan. 31, 1966 [GB] United Kingdom ............... 4178/66
Mar. 7, 1966 [GB] United Kingdom ............... 9764/66

[51] Int. Cl.³ .......................................... C08G 65/38
[52] U.S. Cl. .................................. 528/125; 528/126; 528/128; 528/174; 528/220; 528/223; 528/391
[58] Field of Search ............... 260/49, 47 R, 47 ET; 528/220, 223, 391, 125, 126, 128, 174

[56] References Cited

U.S. PATENT DOCUMENTS 3,886,121  5/1975  Yazi et al. ............................. 260/49

*Primary Examiner*—Lester L. Lee
*Attorney, Agent, or Firm*—Cushman, Darby & Cushman

[57] ABSTRACT

Aromatic polymers containing benzenoid groups and oxygen atoms in the polymer chains are made by the action of an alkali metal hydroxide on a dihalogenobenzenoid compound in which each halogen atom is activated by an inert electron-attracting group such as $-SO_2-$. When a bis-(4-halogenophenyl) sulphone is reacted with an alkali metal hydroxide, the alkali metal salt of a 4-(4-halogenophenylsulphonyl)phenol is formed as a readily isolated intermediate which polymerizes in the presence or absence of solvent to give a polymer having repeating units of the structure

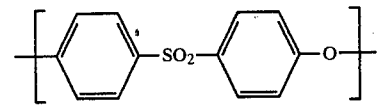

11 Claims, 2 Drawing Figures

PRODUCTION OF POLYARYLENE ETHER SULPHONES AND KETONES

This is a division, of application Ser. No. 335,902 filed Feb. 26, 1973, now U.S. Pat. No. 4,051,109, which in turn is a continuation-in-part of our application Ser. No. 580,290 filed on Sept. 19, 1966, now abandoned.

This invention relates to the production of aromatic polymers and intermediates therefor.

According to the invention, aromatic polymers whose molecular chains comprise benzenoid groups and oxygen atoms and substances polymerisable to give such polymers are produced by a method in which a dihalogenobenzenoid compound having each halogen atom activated by an inert electron-attracting group is caused to react with a substantially equivalent amount of an alkali metal hydroxide by the displacement of alkali metal halide in a polar liquid which is an ionising solvent for alkali metal phenoxides and is stable under the reaction conditions employed.

The halogen atoms in the dihalogenobenzenoid compound are preferably chlorine or fluorine. The fluorine derivatives generally are more reactive and enable the displacement of alkali metal halide to be carried out more quickly, but are more expensive. Bromine derivatives are also relatively expensive and although they resemble the chlorine derivatives in performance they would seem to offer no advantages. Iodine derivatives are generally less suitable.

Any dihalogenobenzenoid compound or mixture of dihalogenobenzenoid compounds is suitable for the invention provided the two halogen atoms are linked to benzene rings which have an electron-attracting group, preferably ortho or para to the halogen atom. The dihalogenobenzenoid compound can have the halogen atoms linked to the same benzenoid ring or to different benzenoid rings, so long as each is activated by an electron-attracting group.

Any electron-attracting group inert under the conditions of the reaction can be used as the activated group in these compounds. The more powerful electron-attracting groups give the highest reaction rates and are therefore preferred. Electron-donating groups should also be absent from the same benzenoid ring as the halogen. It may be a univalent group that activates one or more halogen atoms in the same ring, for example a nitro, phenysulphenyl, alkylsulphonyl, cyano, trifluoromethyl or nitroso group, or heteronitrogen as in pyridine; or it may be a bivalent group that can activate halogen atoms in two different rings, for example a sulphone, sulphoxide, azo, carbonyl, vinylene, vinylidene, tetrafluoroethylene or organic phosphine oxide group; or it may be a bivalent group that can activate halogen atoms on the same ring, as in the case of difluorobenzoquinone and 1,4-, 1,5- or 1,8-difluoroanthraquinone.

In particular, the dihalogenobenzenoid compound may have the formula

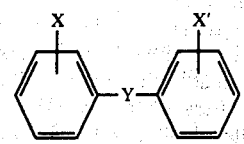

in which X and X' are conveniently the same but may be different and are halogen atoms, and Y is —SO$_2$—, —SO— or —CO— or a radical of the formula —Y'—A—Y"— in which Y' and Y" may be the same or different and each is —SO$_2$—, —SO— or —CO— and A is a bivalent oganic radical, which may be aliphatic, aromatic or heterocyclic and has both valencies linked to carbon atoms. For example A may be a bivalent aromatic radical derived from benzene, a fused-ring aromatic hydrocarbon containing not more than two aromatic rings (for example naphthalene, indene, fluorene or dibenzofuran), or a compound of the formula

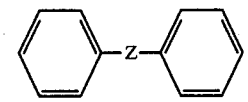

in which Z is a direct link, —O—, —S—, —SO$_2$—, —CO—, a bivalent hydrocarbon or substituted hydrocarbon radical (e.g. alkylene, alkylidene or a bivalent cycloaliphatic or aromatic radical), or a residue of an organic diol (i.e. the bivalent radical obtained by removing the hydrogen atoms from the two hydroxy groups). The halogen atoms in the dihalogenbenzenoid compounds are preferably in the para position to the bridging group Y, because the essentially all-para polymers that can be made from them have better physical properties as thermoplastic materials.

Lower alkyl, alkoxy or alkylthio groups may be present as substituents on any of the aromatic rings but are preferably absent from the halogen-bearing rings and are also preferably absent altogether when the aromatic polymer is required to be stable at high temperatures.

If desired the polymers can be prepared from mixtures of two or more dihalogenobenzenoid compounds, and these may contain different electron-attracting groups.

It has been found that polymers having desirable physical properties, espcially a high softening point, may be made by a method as described above in which a bis-(halogenophenylsulphonyl) benzenoid compound, alone or together with another dihalogenobenzenoid compound is caused to react with an alkali metal hydroxide by the displacement of alkali metal halide. In particular the bis-(halogenophenylsulphonyl) benzenoid compound may have the formula $$X—C_6H_4—SO_2—Ar—SO_2—C_6H_4—X$$

in which X is a halogen atom and Ar is a bivalent aromatic radical derived from enzene, biphenyl, terphenyls, or a fused-ring aromatic hydrocarbon containing not more than three aromatic rings (for example naphthalene, indene, fluorene or dibenzofuran).

The halogen atoms are preferably para to the sulphone groups, although at least some may be ortho.

The other dihalogenobenzenoid compound that may be copolymerised with the bis-(halogenophenylsulphonyl) benzenoid compound may be any of those described above and in particular may conveniently be a bis-(4-halogenophenyl) sulphone.

The alkali metal cation associated with the hydroxide anion is conveniently potassium or sodium. Displacement of alkali metal halide often occurs more readily if the potassium cation is present in the reagent used, but the weight (and usually the price)per mole of a potassium compound is higher than for the corresponding sodium compound. Some or all of the alkali metal cation in the reagent may be replaced by an organic onium cation having a positively charged heteroatom (for example a quaternary ammonium cation such as tetramethylammonium) stable under the conditions of the reaction, and the term "alkali metal salt" as used herein is deemed to refer also to salts containing such onium cations.

In the reaction of the invention, one mole of the dihalogenobenzenoid compound is used for two moles of the alkali metal hydroxide; i.e. the reagents are used in substantially equivalent amounts. Should one of the reagents suffer some decomposition or otherwise be lost from the reaction mixture it may be added initially in slight excess.

Suitable polar liquids for the reaction include: the lower dialkyl and cyclic alkylene sulphoxides and sulphones (e.g. dimethyl sulphoxide and 1,1-dioxothiolan), nitriles (e.g. benzonitrile), diaryl ketones (e.g. benzophenone), diaryl sulphoxides and sulphones, ethers (e.g. dioxane, diethylene glycol dimethyl ether, diphenyl ether, methoxyphenyl ethers), non-olefinic tertiary alcohols (e.g. t-butanol), and water. Mixtures of such substances may conveniently be used, e.g. when one or more components of the mixture would otherwise be solid at the reaction temperature. The liquid (or mixture of liquids) should preferably be a solvent also for the dihalogenobenzenoid compound and preferably also for the alkali metal hydroxide. The amount of the liquid is relatively unimportant provided it is sufficient to dissolve alkali metal salts of phenols produced in the reaction and is not too large to be economically disadvantageous. The total amount of solvent used is desirably sufficient to ensure that none of the starting materials are in the solid state in the reaction mixture. The liquid initially present in the reaction medium need not be the same as that present during the final formation of the polymer. The original liquid may be allowed to remain during the reaction with the subsequent addition of any desired solvents, or it may be removed, e.g. by distillation.

Changing the liquid reaction medium may be convenient as it allows the initial use of liquids that would be less suitable for the final stages, being for example inconveniently volatile or unstable at polymerisation temperatures or incapable of dissolving the resultant polymer to the desired extent. For example, dimethyl sulphoxide is a convenient solvent but cannot be used at such high temperatures as 1,1-dioxothiolan (cyclic tetramethylene sulphone) which may therefore be substituted for it during the reaction.

The liquid reaction medium need not contain any solvent for polymer of high molecular weight even at the later stages of the reaction, although if it does not the product is of relatively low molecular weight unless the final stage of polymerisation is carried out in the melt; this may be explained if the molecular chains of the polymer cease to grow in the solid state.

For the production of low polymer, the polar liquid may conveniently be water or a mixture of water and another liquid or liquids stable to heat under alkaline conditions. The dihalogenobenzenoid compounds are generally immiscible with water and the reaction mixture therefore usually consists of two phases. Vigorous stirring and the use of a suitable emulsifier are then helpful in maximising the interfacial area and hence reaction rate.

The rate of polymer formation in the reaction of the invention rises with rise of temperature and below 200° C. is usually uneconomically slow (although lower temperatures can be used e.g. with bis-(4-fluorophenyl) sulphone). It may however be advantageous to preheat the reaction mixture between 150° C. and 200° C. until inorganic hyroxide anions are no longer present and then raise the temperature to produce the polymer. Temperatures up to 400° C. may be employed, and 250°–250° C. is usually convenient.

The reaction should initially be carried out under pressure if necessary to prevent the escape of dihalogenobenzenoid compound and any volatile solvent or cosolvent. Heating in vacuum may however be desirable at a later stage to remove unwanted solvents, e.g. dimethyl sulphoxide which decomposes at the temperatures required to produce high polymer e.g. from bis-(4-chlorophenyl) sulphone.

The vessel used should be made of or lined with a material that is inert to alkali metal hydroxides and also to alkali metal halides under the conditions employed. For example, glass is unsuitable as it tends to react with hydroxide anion at high temperatures, upsetting the stoichiometry of the polymerisation and contaminating the product with silicate. Some grades of stainless steel undergo surface crazing at these temperatures in the presence of alkali metal halide, and vessels made of or lined with titanium or nickel or an alloy thereof or some similarly inert material would be preferable.

The polymerisation must be concluded under substantially anhydrous conditions to obtain products of high molecular weight. Water is formed in the reaction when an alkali metal hydroxide is used, and must then be removed, conveniently by distillation, e.g. direct or by azeotropic distillation. Any inert volatile liquid that forms an azeotropic mixture with water may be used; benzene, xylene and halogenated benzenes are convenient examples. This liquid need not itself be thoroughly removed after all the water has gone.

It is often advantageous to keep the temperature below 150° C. (preferably at about 100°–140° C.) until all water has been removed, and then to conclude the reaction at a temperature between 150° C. and 350° C.

The reduced viscosity of the polymer is desirably at least 0.3 (measured at 25° C. at 1% in a solvent such as dimethyl formamide) if it is to serve for structural purposes.

To neutralise any reactive oxygen-containing anions, a reagent therefor may be introduced at the termination of the polymerisation. Reactive monofunctional halides, for example methyl chloride, are particularly suitable.

It has been found that an alkali metal salt of a 4-(4-halogenophenylsulphonyl)phenol or 4-(4-halogenobenzoyl)phenol and hence the phenol itself are surprisingly readily obtained by the action of an alkali metal hydroxide on a bis-(4-halogenophenyl) sulphone or ketone in a polar liquid which is an ionising solvent for the phenoxide and is stable under the conditions employed. Very little salt of bis-(4-hydroxyphenyl) sulphone or ketone is formed, except in the presence of excess alkali at high temperatures, because the second halogen atom in the bis-(4-halogenophenyl) sulphone or ketone is unexpectedly much less susceptible than the first to alkaline hydrolysis, and the desired salt of a 4-(4-halogenophenylsulphonyl)phenol or 4-(4-halogenobenzoyl)phenol can be isolated in excellent yield.

Such salts in the solid state are novel and have been found to be valuable intermediates for the production of aromatic polymers, the molecular chains of which comprise para-phenylene groups, oxygen atoms, and sulphone or ketone groups. When such a salt is heated at or above its melting point in the substantial absence of any diluent reactive under the conditions employed, polymer of high molecular weight can be obtained with the elimination of alkali metal halide. The starting material need not consist of a pure reagent but may comprise such materials mixed with each other and/or mixed with some preformed low polymer.

The reaction to produce this polymerisable salt may be carried out at temperatures up to 200° C. but is preferably carried out below 150° C. because above this temperature some polymer or some alkali metal sat of the bisphenol or both may be formed. Temperatures above room temperature and preferably above 60° C. are desirable for the reaction to occur at an economic rate. With a liquid in which both starting materials are soluble, 100°–140° C. is generally convenient although lower temperatures can readily be used with bis-(4-fluorophenyl) sulphone. However, with water alone (which is not a solvent for the dihalogenobenzenoid compound), temperatures above 150° C. are convenient so that the dihalogenobenzenoid compound is molten.

The alkali metal salt of the phenol is initially obtained dissolved in the reaction medium and is preferably isolated directly, although for the purpose of purification it may be more convenient in some cases to acidify and then isolate the free phenol. This can be converted back into an alkali metal salt by treatment with a suitable base (e.g. an alkali metal hydroxide or alkoxide).

A 4-(4-halogenophenylsulphonyl)phenol or 4-(4-halogenobenzoyl)phenol is a useful product in its own right, possessing a halogen atom as well as the phenolic group, and can serve as a valuable chemical intermediate. For example the halogen atom can be replaced by amino or substituted amino groups giving a wide variety of materials.

The polymeric products of low molecular weight which may be produced by the method of the invention e.g. those formed in the presence of water or at temperatures below 200° C. also may find industrial uses directly, for example as sizes and finishes or as lubricant additives or thickeners for non-aqueous liquids. Products with a prepondernace of halogen end-groups or of anionic oxygen-containing end-groups may be prepared by employing a slight excess of the dihalogenobenzenoid compound or of the alkali metal hydroxide respectively. The anionic end-groups may of course be converted into phenolic groups by acidification.

The low polymers are also useful as intermediates for the production of various high polymers. A low polymer with predominantly anionic end-groups, for example, can react with a benzenoid compound containing at least three activated halogen atoms to give a thermoset material. Free phenolic end-groups may be linked further in conventional manner, e.g. with diisocyanates.

If the stoichiometry of the initial reaction is carefully preserved, so that activated halogen end-groups and anionic oxygen-containing end-groups are present in approximately equal numbers in the low polymers, these can be converted (like the alkali metal salts of the halogenophenols described above) directly into thermoplastic high polymers by heating at 200°–400° C. (preferably 250°–350° C.) in the substantial absence of water or any other liquid diluent reactive under the conditions employed. This reaction is conveniently carried out in an extruder.

The alkali metal halide resulting from the initial reaction with the dihalogenobenzenoid compound need not be removed before the subsequent anhydrous heating; together with further alkali metal halide formed in the latter step it can all be removed from the resultant high polymer by any suitable means. For example, it can be extracted from the high polymer using water, or the polymer itself can be dissolved in a strongly polar organic solvent (for example dimethyl formamide, 1-methyl-2-oxo-pyrrolidine, dimethyl sulphoxide, 1,1-dioxothiolan or nitrobenzene) and then reprecipitated by addition to a liquid such as water which is miscible with the polymer solvent but itself a non-solvent for the polymer.

When the polymer is formed in solution, a convenient procedure is to add the reaction mixture (which may be decanted or filtered from solid alkali metal halide) to an excess of a liquid which is miscible with the reaction solvent but in which the polymer is insoluble. If the reaction solvent is water-miscible, or is miscible with a liquid in which residual alkali metal halide also dissolves, the polymer can thus be obtained in one step. Otherwise, as for example if the reaction mixture is poured into methanol, the precipitated polymer initially contains alkali metal halide which can subsequently be washed out with water.

It has also been found that products having especially desirable physical properties may be made by a method as described above in which an alkali metal salt of a 4-(4-halogenobenzoyl)phenol is copolymerised with an alkali metal salt of a 2-(4-halogenobenzoyl)phenol or an alkali metal salt of a 4-(4-halogenophenylsulphonyl) phenol by the displacement of alkali metal halide. The physical properties of these polymers are closely dependent on their crystallisation characteristics, e.g. degree of crystallinity, crystal form, rate of crystallisation and melting point. The all-para polyketone having repeating units of the formula I

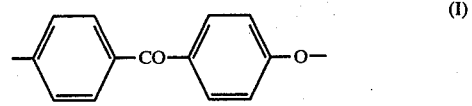

is a highly crystalline and rather intractable material, and the presence of repeating units of the formula II or III

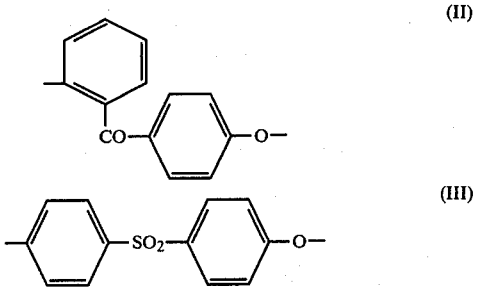

in the copolymers made according to the invention correspondingly reduces the tendency of the products to crystallise and also their melting points.

The polymerisations are preferably carried out in dimethyl sulphone solution at 200°–250° C. in the absence of water and oxygen. Polymerisations in 1,1-dioxothiolan solution at 240° C. tend to yield polymers of low molecular weight. Polymerisations in the absence of solvents at 320°–340° C. tend to form insoluble material; they may also isomerise units II into the para configuration I thus allowing copolymers of the invention to be produced from monomer units II alone.

The present invention provides a means of controlling the crystallinity of aromatic polymers the chains of which comprise para-phenylene groups, oxygen atoms and carbonyl groups by replacing some of the para-phenylene groups by ortho-phenylene groups and/or replacing some of the carbonyl groups by sulphonyl groups; thus it is possible by replacing a predetermined proportion of such groups to adjust the crystallisation characteristics of the various products to give the physical properties most suitable for particular purposes.

Tables 1 and 2 show the structures of examples of copolymers prepared by polymeristions according to the invention in which both monomers were initially present in the reaction mixture, in comparison with the homopolymers of each monomer.

TABLE 1.

| Copolymers of units I and II | |
|---|---|
| Ratio of I to II | Structure 'as made' |
| 0/100 | Amorphous |
| 20/80 | Crystalline |
| 35/65 | Crystalline |
| 50/50 | Crystalline |
| 65/35 | Crystalline |
| 80/20 | Crystalline m.p. 312° C. |
| 100/0 | Crystalline m.p. 338° C. |

'As made' i.e. not after any annealing treatment likely to increase crystallinity Crystallinity was detected by X-ray diffraction. Melting points were determined using a Perkin-Elmer differential scanning calorimeter on a 5 mg sample with a heating rate of 16 deg C./min. and are corrected by calibration.

TABLE 2.

| Copolymers of units I and III | |
|---|---|
| Ratio of I to III | Structure 'as made' |
| 0/100 | Amorphous |
| 20/80 | Amorphous |
| 35/65 | Amorphous |
| 50/50 | Crystalline m.p. 295° C. |
| 65/35 | Crystalline |
| 75/25 | Crystalline |
| 80/20 | Crystalline |
| 100/0 | Crystalline m.p. 338° C. |

The crystal forms exhibited by these copolymers are very similar to that of poly(4,4'-diphenylene ether ketone)

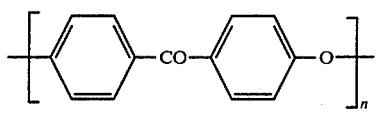

and, as reported in Dutch application No. 6,408,130, the regular alternating copolymer

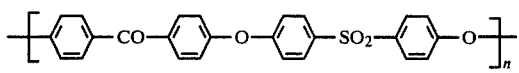

is almost certainly amorphous. Hence, the copolymers made by the present invention are thought to contain poly(4,4'-diphenylene ether ketone) blocks.

Random copolymers may be readily obtained by slowly feeding the alkali metal salt of the 2-(4-halogenobenzoyl)phenol or 4-(4-halogenophenylsulphonyl)phenol into a reaction mixture which initially contained only the alkali metal salt of the 4-(4-halogenobenzoyl)phenol. Crystalline random copolymers, prepared in this way, generally have lower melting points than the block copolymers of the same composition.

Two types of copolymer are of major interest:

(a) Crystalline (random or block) copolymers with m.p. 250°-300° C. for application as thermoplastic, fibre-forming or film-forming materials.

(b) Copolymers which are amorphous 'as made' but which crystallise on annealing or on nucleation, e.g. with poly-(4,4'-diphenylene ether ketone). Such polymers may be cast into films or spun into fibres from the solutions in which they are prepared or may be isolated as amorphous polymers and processed as such in the manner customary, e.g. for polyethylene terephthalate films and fibres. Among the copolymers that may exhibit this behaviour are random copolymers or block copolymers within the approximate composition ranges II/I=20/80 and III/I=35/65 to 50/50.

The following examples illustrate the invention.

EXAMPLE 1

Bis-(4-chlorophenyl) sulphone (14.36 g; 0.05 mole), aqueous 43.6% w/w potassium hydroxide solution (12.88 g; 0.10 mole KOH), and 1,1-dioxothiolan (100 cm$^3$) were stirred vigorously under nitrogen at 140° C. for 4 hours in a vessel fitted with a reflux condenser. Xylene (15 cm$^3$) was then added, the reflux condenser was replaced by a Dean & Stark apparatus, and the mixture was boiled until all water (about 7 cm$^3$) was removed azeotropically (this took about 3 hours). Xylene was then distilled off and the temperature of the reaction vessel was raised to 240° C. After 7 hours the product was cooled to about 150° C. and a stream of methyl chloride was passed through the vessel for about 10 minutes. The solution in the reaction vessel was then decanted from solid potassium chloride through a sintered glass filter into ethanol (1 dm$^3$) with vigorous stirring. The precipitated polymer was washed several times with water and with ethanol and dried overnight at 100° C. in high vacuum.

A fibre could be drawn from the molten polymer.

EXAMPLE 2

Polymers may similarly be obtained as in Example 1 from bis-(4-fluorophenyl) sulphone, bis-(4-chlorophenyl) sulphoxide, 4,4'-dichlorobenzophenone, 4,4'-bis-(4-chlorophenylsulphonyl)biphenyl, and 4-(4-chlorophenylsulphonyl)phenoxy-4'-chlorobenzophenone.

EXAMPLE 3

Bis-(4-chlorophenyl) sulphone (14.35 g; 0.05 mole), aqueous potassium hydroxide solution (12.88 g; 0.10 mole of KOH) and dimethyl sulphoxide (100 cm$^3$) were stirred together in a stainless steel reaction vessel under a blanket of nitrogen for 24 hours at 100° C. Benzene (140 cm$^3$) was added and water (7 cm$^3$) was removed as benzene-water azeotrope and then most of the benzene was removed by distillation.

1,1-Dioxothiolan (100 cm$^3$) was added and dimethyl sulphoxide was distilled off at 50° C. under reduced pressure (1.5 torr). When the dimethyl sulphoxide had been removed, the mixture was stirred under nitrogen at 220° C. for 24 hours, cooled, and poured into ethanol.

The precipitated product was washed with ethanol and water and dried to yield a polymer (11.4 g) of reduced viscosity 0.10 at 1% in dimethyl formamide at 25° C.

EXAMPLE 4

Bis-(4-chlorophenyl) sulphone (287 g; 1 mole), potassium hydroxide (112 g; 2 moles) and water (1.7 dm$^3$) were shaken in a stainless steel autoclave for 18 hours at 195°–200° C. The product was cooled and added to water (5 dm$^3$) when some solid was formed. Dilute sulphuric acid was added until the pH was below 2.0 and more solid was precipitated. The whole was extracted with diethyl ether (2 dm$^3$), after which a solid remained suspended in the aqueous phase. This solid was filtered off, washed with water and dried to give a polymer (12 g) shown by infra-red spectroscopy to contain units of the formula

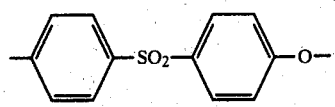

Monomeric material was isolated from the ethereal phase as follows. Potassium hydroxide solution (1.0 H, 2 dm$^3$) was added to extract phenolic material from residual bis-(4-chlorophenyl) sulphone (of which 0.15 mole was recovered). The aqueous alkaline solution was then acidified with concentrated hydrochloric acid to precipitate a mixture of phenolic material (170 g) which separated as a gum. This was digested with hot chloroform (0.75 dm$^3$) leaving a residue of bis-(4-hydroxyphenyl) sulphone (71 g; 0.28 mole) identified by infra-red spectroscopy. The solution was evaporated to yield 4-(4-chlorophenylsulphonyl)phenol (99 g; 0.37 mole) identified by infra-red spectroscopy.

EXAMPLE 5

The rate of hydrolysis of bis-(4-chlorophenyl) sulphone (14.36 g; 0.05 mole) in the presence of 45% w/w aqueous potassium hydroxide (26 g; 0.20 mole KOH) in solution in dimethyl sulphoxide (100 cm$^3$) was studied at 100° C., 120° C. and 140° C. The extent of hydrolysis was measured by gravimetric estimation of chloride ion at various reaction times. In FIG. 1 of the accompanying drawings, the results are presented as a graph in which the abscissa is the reaction time in hours and the ordinate is the amount of chloride ion as a percentage of the total amount of chlorine substituent in the bis-(4-chlorophenyl) sulphone.

At 140° C., complete hydrolysis was occurring. At 120° C. the two chlorine substituents were clearly being hydrolysed at different rates, and at 100° C. hydrolysis beyond the half-way stage was very slow. The second chlorine substituent was hydrolysed only at about one-hundredth the rate of the first. In this experiment there were two liquid phases present initially but only one phase during the latter part of the hydrolysis.

EXAMPLE 6

Figure 2:
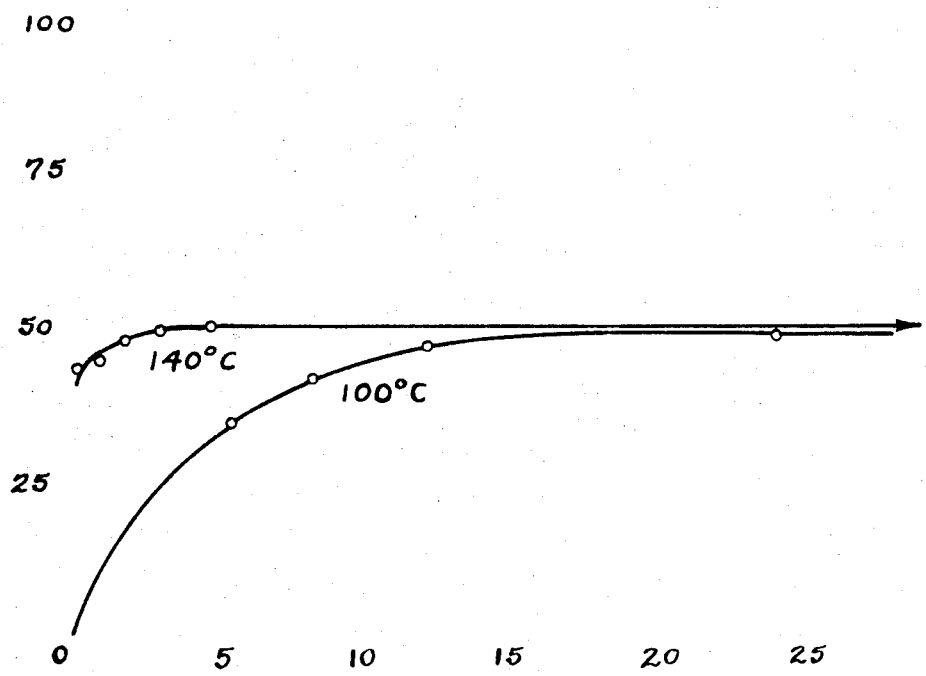

The experiment described in Example 5 was repeated using only two molar equivalents of potassium hydroxide. Two liquid phases were present throughout. In FIG. 2 of the drawings, where the abscissa and ordinate are as in FIG. 1, the results show that the removal of the chlorine substituent from potassium 4-(4-chlorophenylsulphonyl)phenoxide, either by formation of polymer or by hydrolysis to give the bisphenol and potassium chloride, in very slow at 100° C. and at 140° C. over 24 hours, since the curves for both these temperatures virtually level off with time at the stage of 50% formation of chloride ion.

EXAMPLE 7

The experiments described in Examples 5 and 6 were repeated using 1,1-dioxothiolan instead of dimethyl sulphoxide as solvent. The hydrolysis appeared to proceed more slowly, in spite of vigorous stirring. Two liquid phases were present throughout both experiments.

EXAMPLE 8

Pure bis-(4-chlorophenyl) sulphone (359 g; 1.25 mole), potassium hydroxide solution (64 g; containing 5.0 moles of KOH), and dimethyl sulphoxide (2.5 dm$^3$) were stirred under nitrogen in a stainless steel vessel for 5 hours at 100° C. and then poured into water (10 dm$^3$). The milky solution was acidified with nitric acid and 4-(4-chlorophenylsulphonyl)phenol precipitated; analysis of the solution for chloride ion showed 51.3% hydrolysis of the chlorine substituents in the starting material. The 4-(4-chlorophenylsulphonyl)phenol was extracted into ether. The ether solution was extracted with aqueous sodium hydroxide (to separate phenolic material from any unhydrolysed starting material), and the sodium hydroxide solution was acidified once again to give 4-(4-chlorophenylsulphonyl)phenol (320 g; 95.5% yield), m.p. 143°–145° C., probably contaminated with a little bis-(4-hydroxyphenyl) sulphone. The product was dissolved in hot toluene, in which the bis-phenol is sparingly soluble (about 0.1%), filtered hot and allowed to crystallise. Recrystallisation was carried out from chloroform containing active charcoal and yielded a product of m.p. 145°–146° C. It was soluble in cold aqueous potassium hydroxide, sodium carbonate or potassium carbonate but insoluble in warm aqueous sodium bicarbonate and (like phenol itself) was precipitated from its solution in potassium hydroxide by carbon dioxide.

The potassium salt was isolated as a yellowish powder, m.p. 274°–276° C., by the reaction of an ethanolic solution of 4-(4-chlorophenylsulphonyl)phenol with an equimolar amount of potassium ethoxide (under anhydrous conditions) or of aqueous potassium hydroxide. The salt was soluble in cold dimethyl formamide, cold dimethyl sulphoxide, warm 1,1-dioxothiolan, warm ethanol and hot nitrobenzene. Exposure of the salt to the atmosphere (relative humidity about 50%) resulted in a weight increase of 5% in 90 minutes, corresponding to the formation of a monohydrate, and the colour changed from yellow to pure white.

To prepare a polymer, the potassium salt of 4-(4-chlorophenylsulphonyl)phenol (3.07 g; 0.01 mole) was heated in an evacuated glass tube for 1 hour at 300° C. The tube was cooled and broken open. The product was crushed and warmed with dimethyl formamide (30 cm$^3$), in which potassium chloride is largely insoluble, to dissolve the polymer. The solution was filtered and poured into water (150 cm$^3$) with vigorous agitation. The precipitate was washed with water and dried to give a colourless polymer (2.2 g) having a reduced viscosity of 0.60 in a 1% solution in dimethyl formamide at 25° C.

EXAMPLE 9

Aqueous potassium hydroxide (26.00 g; containing 0.20 mole KOH) was added to a solution of bis-(4-chlorophenyl) sulphone (28.7 g; 0.1 mole) in dimethyl sulphoxide (200 cm$^3$) in a stainless steel vessel. The mixture was stirred under nitrogen for 24 hours at 100° C. Water and dimethyl sulphoxide were removed by distillation at about 1 torr while the temperature was raised to about 180° C. The last traces of dimethyl sulphoxide were removed by crushing the product and heating it at about 180° C. for 2 hours at about 10$^{-3}$ torr.

The dried solid was heated at 300° C. for 30 minutes in a stainless steel vessel under nitrogen. After cooling, the product was crushed and warmed with dimethyl formamide (300 cm$^3$) to dissolve the polymer while potassium chloride and a small amount of resin remained undissolved and were filtered off. The solution was poured into water (1500 cm$^3$) with vigorous agitation. The precipitate was washed with water and dried to give a colourless polymer (16.5 g) having a reduced viscosity of 0.49 in a 1% solution in dimethyl formamide at 25° C.

The polymer was compression-moulded at 320° C. for 5 minutes to give a tough transparent film.

EXAMPLE 10

Bis-(4-chlorophenyl) sulphone was hydrolysed as described in Example 9 by aqueous potassium hydroxide in dimethyl sulphoxide over 24 hours at 100° C. The solution so obtained was cooled to room temperature and decanted through a filter to remove potassium chloride: on the assumption that the potassium salt of 4-(4-chlorophenylsulphonyl)phenol had been produced, this removed 97% of the potassium chloride formed, the rest stayed in solution. The resulting mobile yellow solution was placed in a rotary evaporator and the pressure was reduced to below 1 torr as the temperature was progressively raised over 8 hours to 240° C. to distil off the dimethyl sulphoxide. The product remaining was a yellow solid containing about 40% of the potassium salt of 4-(4-chlorophenylsulphonyl)phenol, about 60% of a low polymer of reduced viscosity 0.06 (in a 1% solution in dimethyl formamide at 25° C.), about 0.4% of dimethyl sulphoxide, and other substances in low concentration.

This product (11.5 g) was polymerised at 280° C. for 30 minutes in a glass tube which was continuously evacuated by a high-vacuum pump. The volatile substances evolved were collected (0.06 g) and consisted of about 40% water and 60% dimethyl sulphoxide. The solid product from the polymerisation was crushed and warmed with dimethyl formamide (100 cm$^3$) and filtered to remove insoluble material; this was entirely potassium chloride and no insoluble polymer was present. The solution of polymer in dimethyl formamide was poured with stirring into water (1 dm$^3$) to precipitate the polymer, which was washed with water and then with methanol and dried in vacuum at 150° C. The product (8.6 g; 99% yield) had a reduced viscosity of 0.52 in a 1% solution in dimethyl formamide at 25° C., and gave a strong tough compression moulding.

A similar polymerisation carried out without continuous evacuation (i.e. without continuous removal of dimethyl sulphoxide or some harmful decomposition product) yielded a polymer of bad odour and colour and of lower molecular weight but containing up to 20% of polymeric material (probably cross-linked) insoluble in dimethyl formamide.

EXAMPLE 11

Bis-(4-chlorophenyl) sulphone was hydrolyzed as described in Example 3 by aqueous potassium hydroxide in dimethyl sulphoxide over 24 hours at 100° C. The solution in dimethyl sulphoxide was cooled and decanted from solid potassium chloride and 1,1-dioxothiolan (35 cm$^3$) was added. Dimethyl sulphoxide was removed by distillation at 10 torr and some 1,1-dioxothiolan was allowed to distil to sweep away the last trace of dimethyl sulphoxide. Distillation was continued until the product was an 80% w/w solution of the crude potassium salt of 4-(4-chlorophenylsulphonyl)phenol in 1,1-dioxothilan. When cold, the solution solidified as a brittle material completely soluble in water.

When this material was heated in nitrogen for 7 hours at 240° C., a polymer was formed having a reduced viscosity of 0.22 (in a 1% solution in dimethyl formamide at 25° C.). If the material was first diluted with 1,1-dioxothiolan to give a concentration of 45%, heating under similar conditions yielded a polymer of reduced viscosity 0.18. In neither case was any polymer formed insoluble in dimethyl formamide.

EXAMPLE 12

A solution of the potassium salt of 4-(4-chlorophenylsulphonyl)phenol in dimethyl sulphoxide was prepared and decanted from potassium chloride as described in Example 10. Most of the water and dimethyl sulphoxide were then removed by distillation at 25 torr, and when cold the product was powdered and placed in a rotary evaporator and the temperature was raised to 260° C. while the pressure was 0.1 torr. The product was a hard brittle prepolymer containing about 99% low polymer (reduced viscosity 0.2 at 1% in dimethyl formamide at 25° C.) and about 1% of the potassium salt of 4-(4-chlorophenylsulphonyl)phenol; the concentration of dimethyl sulphoxide was less than 0.1% and probably less than 0.01%.

This prepolymer (5.0 g) was heated in vacuo for 30 minutes at 280° C. in a glass tube. It was then cooled and dissolved in dimethyl formamide and separated from potassium chloride which was filtered off. The polymer was precipitated by adding the solution to water: the product (3.5 g) had a reduced viscosity of 0.58 g (in a 1% solution in dimethyl formamide at 25° C.), and no polymer was formed insoluble in dimethyl formamide.

The prepooymer (5.0 g), when heated in nitrogen for 30 minutes at 280° C. in a glass tube and worked up as before, yielded a polymer (3.6 g) of reduced viscosity 0.62. No insoluble polymer was formed.

The prepolymer (5.0 g) and 1,1-dioxothiolan (6.1 g) were stirred together and the temperature was raised to 220° C., when all the prepolymer appeared to have dissolved and the concentration of the solution was about 45% w/w. Further polymerisation was carried out at 240° C. for 4 hours; the solution was cooled and water was added to precipitate a polymer (3.7 g after washing and drying) having a reduced viscosity of 0.42.

EXAMPLE 13

Pure bis-(4-chlorophenyl) sulphone (14.36 g; 0.05 mole), aqueous sodium hydroxide (8.99 g; 0.10 mole NaOH), and dimethyl sulphoxide (100 cm$^3$) were stirred under nitrogen for 24 hours at 100° C. in a stainless steel vessel. A tandem experiment showed that 48.2% of the chlorine initially present in the bis-(4-chlorophenyl) sulphone was present as chloride anion under these reaction conditions.

Most of the dimethyl sulphoxide and water were removed by distillation at 20 torr, and the product was finally dried in a rotary evaporator at a temperature rising to 270° C. at a pressure of 0.1 torr. The product was a yellow powder comprising about 20% of very low polymer and about 80% of the sodium salt of 4-(4-chlorophenylsulphonyl)phenol.

This product (10.02 g) was heated for 30 minutes at 300° C. in vacuo and worked up as described in Example 10 to give polymer (6.62 g; 84% yield) of reduced viscosity 0.26 (at 1% in dimethyl formamide at 25° C.). A similar polymerisation carried out at 325° C. gave a polymer (3.81 g; 42% yield) having a reduced viscosity of 0.55, together with a resin (4.20 g) insoluble in dimethyl formamide.

EXAMPLE 14

Pure 4-(4-chlorophenylsulphonyl)phenol (21.87 g; 0.10 mole), prepared as described in Example 8, was dissolved in ethanol (50 cm³) and aqueous sodium hydroxide (54.48 g; 0.10 mole NaOH) was added. The solution was evaporated to dryness at room temperature under reduced pressure and finally dried at 200° C. for 24 hours under high vacuum. The sodium salt of 4(4-chlorophenylsulphonyl)phenol was obtained as an off-white solid of m.p. 320°-325° C. Titration with 0.1 N hydrochloric acid gave the purity as 99%.

This pure sodium salt (0.962 g) was heated in vacuo above 325° C. for 30 minutes. The product was cooled, dissolved in dimethyl formamide and filtered to remove undissolved sodium chloride, and the polymer was precipitated by adding the solution to methanol. The precipitate was washed repeatedly with methanol and water and dried at 120° C. in vacuo to give a polymer (0.75 g; 98% yield) having a reduced viscosity of 0.47 in a 1% solution of dimethyl formamide at 25° C.

EXAMPLE 15

4,4'-Bis-(4-chlorophenylsulphonyl) biphenyl (10.06 g; 0.02 mole) was stirred with aqueous potassium hydroxide (5.12 g of 43.7% solution; 0.04 mole KOH) in dimethyl sulphone (75 g) at 140° under nitrogen in a steel beaker for 92 hours. The solution was concentrated by distilling dimethyl sulphone (53 g) under reduced pressure, and the mixture was polymerised by stirring under nitrogen at 230° for 17 hours. After the polymerised mixture had cooled to room temperature, it was treated with dimethyl formamide and a small quantity of insoluble material was filtered off. The dimethyl formamide solution was poured slowly into stirred water. A polymer having repeating units of the formula

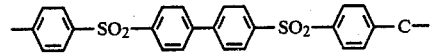

was filtered off, washed with methanol and dried under vacuum.

EXAMPLE 16

4,4'-Bis-(4-chlorophenylsulphonyl)-biphenyl (5.03 g; 0.01 mole) and bis-(4-chlorophenyl)sulphone (11.48 g; 0.04 mole) were stirred with aqueous potassium hydroxide (12.79 g of 43.7% solution; 0.10 mole KOH) in dimethyl sulphoxide (100 cm³) at 140° C. under nitrogen in a steel beaker. When most of the dimethyl sulphoxide had been distilled off, under reduced pressure, and solid began to come out of solution, dimethyl sulphone (80 g) was then added and distillation was continued until dimethyl sulphone (50 g) had been collected. The mixture was then polymerised at about 230° C. for 18 hours under nitrogen. The reaction mixture was allowed to cool and dissolved in dimethyl formamide. The dimethyl formamide solution was poured slowly into stirred water, from which the polymer precipitated. After filtration, the cream-coloured polymer was washed with methanol and dried under vacuum at 100° C. The polymer having repeating units of the formulae

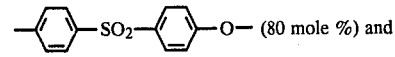

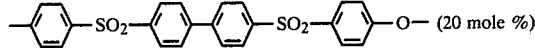

had a reduced viscosity of 0.21, measured at 1% in dimethyl formamide at 25° C.

Other cohydrolyses and polymerisations may be carried out using different molar proportions of 4,4'-bis-(4-chlorophenylsulphonyl)biphenyl and bis-(4-chlorophenyl)sulphone. A polymer having repeating units of the formulae

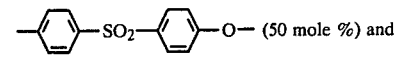

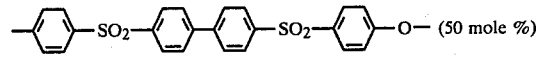

had a Tg of about 300° C. and could be solvent-cast from dimethyl formamide.

EXAMPLE 17

1,3-Bis-(4-chlorophenylsulphonyl) benzene may be hydrolysed or cohydrolysed and polymerised by the methods of Examples 15 and 16 to give polymers having repeating units of the formula

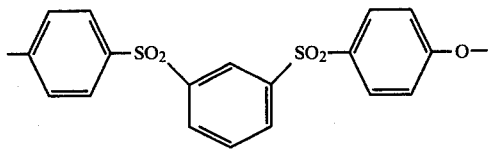

EXAMPLE 18

1,5-Bis-(4-chlorophenylsulphonyl)naphthalene may be hydrolysed or cohydrolysed and polymerised by the methods of Examples 15 and 16 to give polymers having repeating units of the formula

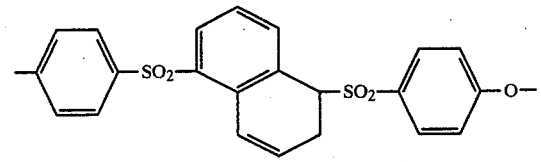

In the following examples reduced viscosities were measured at 1% in dimethyl formamide at 25° C.

EXAMPLE 19

The potassium salts of 4-(4-chlorophenylsulphonyl) phenol (1.00 g) and 4-(4-chlorobenzoyl) phenol (1.00 g) and dimethyl sulphone (2.00 g) were heated together under dry nitrogen for 18 hours at 220° C. The viscous reaction product was allowed to cool and was then diluted with dimethyl formamide. The resulting solution was filtered and then dripped into stirred aqueous methanol (50:50 v/v) and the polymer which precipitated was collected, washed with boiling methanol and then dried in vacuo. The resulting polymer (1.0 g) contained 7.8% sulphur, corresponding to the structure III/I=52/48, and had reduced viscosity=0.22. The polymer was crystalline (m.p. 295° C.) and was stable in air up to 500° C.

EXAMPLE 20

Example 19 was repeated using 7.5 g of dimethyl sulphone. 0.8 g of polymer was obtained with reduced viscosity=0.30.

EXAMPLE 21

The potassium salts of 4-(4-chlorophenylsulphonyl) phenol (1.00 g) and 4-(4-chlorobenzoyl) phenol (1.00 g) and 1,1-dioxothiolan (10.0 cm$^3$) were heated together under dry nitrogen for 4.5 hours at 240°-250° C. The reaction mixture was allowed to cool and was then filtered and dripped into stirred water. The precipitated polymer was collected, washed with boiling methanol and then dried in vacuo to yield 1.8 g of a crystalline polymer having reduced viscosity=0.10.

EXAMPLE 22

The potassium salts of 4-(4-chlorophenylsulphonyl) phenol (1.00 g) and 4-(4-chlorobenzoyl) phenol (1.00 g) were heated together at 320°-340° C. under dry nitrogen for 1 hour. The reaction products were heated with dichloroacetic acid (40 cm$^3$) at 140° C. for 30 minutes and the resulting solution was filtered.

The filtrate was dripped into stirred water and the polymer which precipitated was collected, washed with boiling methanol and dried to yield 0.4 g of an amorphous polymer containing 8.0% sulphur, corresponding to the structure III/I=53/47.

The residue was washed with water and dried to yield 1.6 g of an amorphous solid.

EXAMPLE 23

The potassium salts of 4-(4-chlorobenzoyl) phenol (1.00 g) and 2-(4-chlorobenzoyl) phenol (1 g) and dimethyl sulphone (12 g) were heated together under dry nitrogen for 18 hours at 220° C. The reaction mixture was allowed to cool and was diluted with hot dimethyl formamide. The resulting solution was filtered and then dripped into stirred water. The polymer which precipitated was collected, washed with hot methanol and dried to yield 0.7 g of a crystalline polymer having reduced viscosity=0.18.

EXAMPLE 24

The potassium salt of 2-(4-chlorobenzoyl) phenol (1.00 g) was heated under dry nitrogen at 320°-340° C. for 1 hour. The reaction product was worked up as described in Example 22 to yield, from the filtrate, 0.2 g of a highly crystalline polymer (m.p. 290° C.) and, from the residue, 0.8 g of a crystalline material. A similar polymerisation carried out in solution in dimethyl sulphone yielded an amorphous product (see Table 1).

EXAMPLE 25

Bis-(4-fluorophenyl) sulphone (100 g; 0.394 mole), potassium hydroxide solution (91.98 g; 0.787 mole KOH) and dimethyl sulphoxide (400 cm$^3$) were stirred together in a stainless steel vessel under nitrogen at 57° C. for 24 hours. Two liquid phases remained throughout the reaction. The reaction mixture was diluted with water and twice extracted with diethyl ether to recover non-phenolic material (9 g). The aqueous phase was then acidified and the phenolic component (86 g; m.p. 150°-154° C.) was extracted with more ether. By subliming this product under a diffusion pump at 180° C., followed by recrystallisation from toluene (400 cm$^3$), 4-(4-fluorophenylsulphonyl)phenol (72.5 g) was obtained, m.p. 158°-159° C. The potassium salt was obtained from this phenol as a very pale yellow solid.

A little of the potassium salt was melt-polymerised at 280° C. for 30 minutes with continuous evacuation. No volatile material was evolved and a tough polymer of very good colour was obtained having a reduced viscosity of 0.95.

The potassium salt (13 g) was polymerised in 1,1-dioxothiolan (20 g) for 16 hours at 200° C. The polymer was then end-stopped by adding methyl chloride (0.5 g) in 1,1-dioxothiolan (12 cm$^3$) at 150° C. and the color immediately changed from a pale yellow to an almost white slurry. The system was diluted with dimethyl formamide and the polymer (10.5 g) was reprecipitated with water; it had a reduced viscosity of 0.46 and compression mouldings made at 320° C. for 3 minutes were tough and of excellent colour.

The potassium salt (15 g) was dissolved in redistilled dimethyl sulphoxide (10 cm$^3$). The stirred mixture was heated in a glass vessel maintained at 160° C. for 18 hours under a slow stream of nitrogen. The polymer was end-stopped by bubbling methyl chloride into the stirred mixture at 150° C. The color changed from pale lemon-yellow to white over 5 minutes. After 10 minutes dimethyl formamide was added and the polymer was then precipitated with hot distilled water in a macerator. The product was completely soluble in dimethyl formamide and had a reduced viscosity of 0.40. Compression mouldings were tough and of excellent color, and the polymer was stable in the melt for 35 minutes at 380° C. (2.3 kP).

We claim:

1. A process for preparing an aromatic polymer which comprises heating a condensed oligomer obtained by reaction in a solvent of a dihalo benzenoid compound of the formula

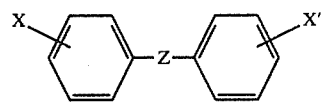

wherein Z represents —SO$_2$ or —CO—; X and X' are halogen atoms which are ortho or para to Z with a substantially equivalent amount of an alkali metal hydroxide followed by removal of solvent; said condensed oligomer being heated at 200°-400° C. under a nonreactive atmosphere in the substantial absence of a solvent.

2. A process for preparing an aromatic polymer which comprises heating a condensed oligomer having a reduced viscosity of 0.06 to 0.2 as measured in a 1% solution of said oligomer in dimethyl formamide at 25° C. obtained by reaction in a solvent of a dihalo benzenoid compound of the formula

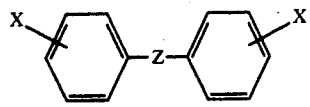

wherein Z represents —$SO_2$— or —CO—; X and X' are halogen atoms which are ortho or para to Z, with a substantially equivalent amount of an alkali metal hydroxide followed by removal of solvent; said condensed oligomer being heated at 200°–400° C. under a nonreactive atmosphere in the substantial absence of a solvent.

3. The process of claim 1 wherein the condensed oligomer is heated at 200°–400° C. in a vacuum in the substantial absence of a solvent.

4. The process of claim 1 wherein the condensed oligomer is heated at 200°–400° C. in an inert gas atmosphere in the substantial absence of a solvent.

5. The process of claim 1, wherein the dihalobenzenoid compound has the formula

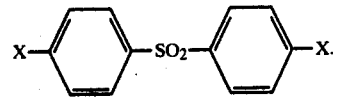

6. A process for preparing an aromatic polymer which comprises heating a condensed oligomer having units having the formula

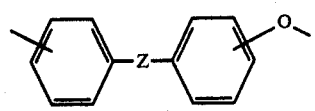

wherein Z represents —$SO_2$— or —CO— and the ether bond is ortho or para to Z; at 200°–400° C. under a nonreactive atmosphere in the substantial absence of a solvent.

7. A process for preparing an aromatic polymer which comprises heating a condensed oligomer having a reduced viscosity of 0.06 to 0.2 as measured in a 1% solution of said oligomer in dimethyl formamide at 25° C. having units having the formula

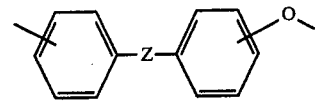

wherein Z represents —$SO_2$— or —CO—; and the ether bond is ortho or para to Z; at 200°–400° C. under a nonreactive atmosphere in the substantial absence of a solvent.

8. The process of claim 6 wherein the condensed oligomer is heated at 200°–400° C. in a vacuum in the substantial absence of a solvent.

9. The process of claim 6 wherein the condensed oligomer is heated at 200°–400° C. in an inert gas atmosphere in the substantial absence of a solvent.

10. The process of claim 6, wherein the condensed oligomer has units having the formula

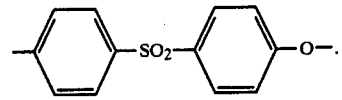

11. The process of claim 6 wherein the condensed oligomer has units having the formula

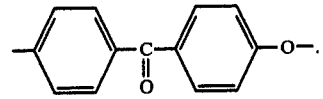

* * * * *